United States Patent [19]

Yamaji

[11] Patent Number: 4,658,032

[45] Date of Patent: Apr. 14, 1987

[54] PROCESS FOR PRODUCING 2,3,5-COLLIDINE AND/OR 2,3,5,6-TETRAMETHYLPYRIDINE

[75] Inventor: Mitsuharu Yamaji, Nara, Japan

[73] Assignee: Koei Chemical Co., Ltd., Osaka, Japan

[21] Appl. No.: 753,533

[22] Filed: Jul. 10, 1985

[30] Foreign Application Priority Data

Jul. 13, 1984 [JP]  Japan .................................. 59-146620

[51] Int. Cl.$^4$ ......................................... C07D 213/127
[52] U.S. Cl. ..................................................... 546/349
[58] Field of Search ......................................... 546/349

[56] References Cited

U.S. PATENT DOCUMENTS

| | | | |
|---|---|---|---|
| 3,354,165 | 11/1967 | Myerly et al. | 546/349 |
| 3,428,641 | 2/1969 | Myerly et al. | 546/349 |
| 3,822,271 | 7/1974 | Lapporte | 546/349 |

FOREIGN PATENT DOCUMENTS 45-25096  8/1970  Japan .................................. 546/349

OTHER PUBLICATIONS

Jour. Amer. Chem. Soc., vol. 86, Dec. 5, 1964, pp. 5355-5356.
Yakugaku Zasshi, vol. 101, No. 1, pp. 20-24 (1981).

*Primary Examiner*—Alan L. Rotman
*Attorney, Agent, or Firm*—Stevens, Davis, Miller & Mosher

[57] ABSTRACT

Process for producing 2,3,5-collidine and/or 2,3,5,6-tetramethylpyridine which is characterized by reacting 3,5-lutidine as the starting material with an aliphatic alcohol having 1 to 4 carbon atoms, in the presence of a catalyst for hydrogenation at a temperature of 200° C. or higher.

The above-mentioned 2,3,5-collidine and/or 2,3,5,6-tetramethylpyridine are important compounds as intermediates for synthesizing various pharmaceutical chemicals.

2 Claims, No Drawings

PROCESS FOR PRODUCING 2,3,5-COLLIDINE AND/OR 2,3,5,6-TETRAMETHYLPYRIDINE

FIELD OF THE INVENTION

The present invention relates to a process for producing 2,3,5-collidine and/or 2,3,5,6-tetramethylpyridine. 2,3,5-Collidine and 2,3,5,6-tetramethylpyridine are important compounds as intermediates for synthesizing various pharmaceutical chemicals.

PRIOR ART

As to processes for producing 2,3,5-collidine and/or 2,3,5,6-tetramethylpyridine, various processes have heretofore been proposed, however none of them are satisfactory as an industrial production process. As, for example, processes for producing 2,3,5-collidine, there are known (1) a process which comprises separating and purifying 2,3,5-collidine from shale oil contained in pitchstone or the like (Bull. Chem. Soc. Japan, 3, 235-242), (2) a process which comprises bringing ammonia into contact with propionaldehyde and acetaldehyde in the presence of alumina at a reaction temperature of 340° C., and thereby obtaining 2,3,5-collidine (Journal der Russishen Physikalischchemischen Gesellschaft,, 61, 2002–2005), (3) a process which comprises allowing methyllithium to react with 3,5-lutidine, and thereby obtaining 2,3,5-collidine (Ber., 88, 1831–1834), etc. However, the above-mentioned process of (1) is industrially disadvantageous because the amount of 2,3,5-collidine contained in the raw material oil shale is very small, so that the amount of the raw material oil shale becomes large. The above-mentioned process of (2) is industrially disadvantageous because the yield of 2,3,5-collidine from propionaldehyde is low. Further, the above-mentioned process of (3) has a narrow use range as an industrial production process because though the yield of 2,3,5-collidine from 3,5-lutidine is about 67%, this process is disadvantageous, for example, in that employment of an organic alkali metal compound which is subjected to decomposition with water or oxygen is thought to be indispensable, so that special care should be taken in handling said compound.

In consideration of such problems of the heretofore well-known techniques, the present inventor has devoted himself to research in order to develop a process for industrially advantageous production of 2,3,5-collidine and/or 2,3,5,6-tetramethylpyridine, and has, at last, accomplished the present invention.

SUMMARY OF THE INVENTION

An object of the present invention is to provide a process for producing 2,3,5-collidine and/or 2,3,5,6-tetramethylpyridine which is characterized by reacting 3,5-lutidine with an aliphatic alcohol having 1 to 4 carbon atoms in the presence of a catalyst for hydrogenation at a temperature of 200° C. or higher.

DETAILED EXPLANATION OF THE INVENTION

As to the catalyst for hydrogenation used in the present invention, there can be exemplified, for example, a Raney cobalt or nickel catalyst prepared by treating a Raney cobalt or nickel alloy with an alkali. In the present invention, it is preferable to use a Raney cobalt catalyst. The Raney cobalt catalyst may contain or need not contain other metals such as manganese and the like. Although the amount of the catalyst for hydrogenation used is not critical, it is suitably in a range of 2 to 80% by weight based on the weight of 3,5-lutidine. Such Raney catalysts are used for the reaction preferably after being more activated by previous contact with hydrogen gas. This activation treatment can be achieved also by charging the Raney catalyst and, if desired, the starting material into a reactor, replacing the air in the reaction vessel with hydrogen, and then carrying out the reaction.

As to the lower alcohol used in the present invention, there may be used any lower alcohol having 1 to 4 carbon atoms such as methanol, ethanol, propanol, butanol or the like.

As to the amount of the lower alcohol used in the present invention, two time or more the molar quantities of 3,5-lutidine used as a starting material is sufficient, though the amount of the lower alcohol is preferably in the range of 2 to 8 times the molar quantities of the 3,5-lutidine. In the present invention, continuous supply of the lower alcohol to the reaction system is preferred. Although the time of continuous supply of the lower alcohol is not critical, a supply time of about 2 to 20 hours is usually efficient. A means for continuously supplying the lower alcohol is not critical, and any well-known means may be used. Concretely, there may be exemplified a method which comprises introducing under pressure the lower alcohol into a reactor containing heated and pressurized 3,5-lutidine by means of a constant volume delivery pump, etc.

As to the reaction pressure, a pressure higher than the vapor pressure of the contents maintained at a definite temperature in a reaction vessel is sufficient, though the reaction pressure is preferably in the range of 10 to 60 $kg/cm^2$. Owing to the continuous supply of the lower alcohol the reaction pressure is increased by a degradation gas produced during the reaction, and if the reaction is continued without taking any measure to counter this, the reaction pressure becomes high, so that the progress of the reaction is inhibited. Therefore, in the present invention, it is preferable to carry out the reaction while maintaining a suitable reaction pressure by allowing said degradation gas to escape out of the reaction system. In allowing said degradation gas to escape out of the reaction system, it is usually advisable to allow non-condensed gas alone to escape by means of a reflux condenser. When no reflux condenser is used, a part of the starting materials and a part of the reaction products are driven out of the reaction system by distillation together with the degradation gas, so that the reaction efficiency is greatly lowered. However, in this invention, the reaction may be carried out also by condensing the starting materials and reaction products driven out of the reaction system by distillation, recovering the same, and returning to the reaction system.

Although no solvent is particularly needed in the present invention, the reaction may be carried out in the presence of an inert solvent. Concrete examples of the inert solvent include benzene, toluene, xylene, etc.

Although in the present invention, the reaction temperature is not critical so long as it is 200° C. or higher, it is preferably in the range of 230° to 270° C. When the reaction temperature is lower than 200° C., the reaction rate of the above-mentioned reaction is greatly lowered, so that industrial disadvantages are brought about. In this invention, when the reaction temperature and/or the reaction time are raised and extended, respectively, the production of 2,3,5,6-tetramethylpyridine can be increased.

In the case of 2,3,5-collidine and/or 2,3,5,6-tetramethylpyridine produced by the above-mentioned process, these desired compounds can easily be separated and purified from the reaction liquid, for example, by removing the catalyst from the reaction liquid by filtration, dehydrating the residue by use of sodium hydroxide or the like, and then distilling the residual oil.

The process of the present invention is advantageous in that the desired compounds 2,3,5-collidine and 2,3,5,6-tetramethylpyridine can be obtained in high yield with respect to the starting material 3,5-lutidine, and that since the reaction is very highly selective, the amount of by-products is small, so that separation and purification of the desired compounds are very easy, therefore 2,3,5-collidine and 2,3,5,6-tetramethylpyridine can be obtained in high purity. Accordingly, said process is industrially very advantageous.

The present invention is specifically explained below by referring to Examples, which are not by way of limitation of the present invention but by way of only illustration.

EXAMPLE 1

Into a 1-liter electromagnetic agitation type autoclave equipped with a reflux condenser were charged 321 g of 3,5-lutidine and 64 g of Raney cobalt, and the air in the vessel was replaced with hydrogen gas, after which the internal temperature was raised to 240° C. Next, 570 g of methanol was continuously introduced thereinto under pressure by means of a constant volume delivery pump over a period of 7 hours. During the introduction of methanol, the produced gas was intermittently liberated outside the reaction system so as to keep the internal pressure of the autoclave in the range of 45 to 60 kg/cm$^2$. After the reaction was completed, the autoclave was cooled to room temperature, and the contents were taken out. The catalyst was removed by filtration, after which 30 g of sodium hydroxide was added to the filtrate, and the resulting mixture was separated by using a separating funnel to obtain 400 g of an oily substance. When the oily substance obtained was distilled by using a Dixon packed tower, there were obtained 32 g of 3,5-lutidine of 99% purity as measured by gas chromatography at a tower top temperature of 90° to 93° C./50 mmHg, 314,4 g of 2,3,5-collidine of 99.3% purity as measured by gas chromatography at a tower top temperature of 102° to 103° C./50 mmHg, and 13.9 g of 2,3,5,6-tetramethylpyridine of 99% purity as measured by gas chromatography at a tower top temperature of 112° C./50 mmHg. The yield of the product 2,3,5-collidine obtained from 3,5-lutidine used as a starting material was 86%, and that of 2,3,5,6-tetramethylpyridine obtained therefrom was 3.4%. The selectivities of the above-mentioned products were 96.3% and 3.7%, respectively.

EXAMPLE 2

Procedures were carried out in the same manner as in Example 1, except that no reflux condenser was used, that the reactants and the reaction products which accompanied the degradation gas was condensed outside the system in the autoclave and collected, and that the degradation gas was continuously liberated outside the system, whereby 358 g of a reaction liquid and 168 g of an accompanying liquid. The reaction liquid was dehydrated and then distilled to obtain 49 g of unreacted 3,5-lutidine, 257 g (yield 71%) of a product 2,3,5-collidine and 9 g (yield 2.3%) of another product 2,3,5,6-tetramethylpyridine. The amount of unreacted 3,5-lutidine contained in the accompanying reaction liquid was 5.6% and that of a product 2,3,5-collidine contained therein was 6.7%. When these facts were put together and calculation was performed from the amount of the starting material 3,5-lutidine consumed, the selectivities for the products 2,3,5-collidine and 2,3,5,6-tetramethylpyridine were 90% and 2.8%, respectively.

EXAMPLE 3

Procedures were carried out in the same manner as in Example 1, except that the reaction temperature was adjusted so as to be in the range of 250° to 260° C., to obtain products 2,3,5-collidine and 2,3,5,6-tetramethylpyridine in yields of 81% and 9%, respectively.

EXAMPLE 4

Procedures were carried out in the same manner as in Example 1, except that Raney nickel was used as a catalyst for hydrogenation, and that the reaction temperature was adjusted so as to be in the range of 240° to 270° C., whereby a product 2,3,5-collidine was obtained in a 30% yield. No production of 2,3,5,6-tetramethylpyridine was observed.

EXAMPLE 5

By a method similar to that of described in Example 4, except that ethanol was used in place of methanol, there was obtained 2,3,5-collidine in a yield of 30%.

EXAMPLE 6

By a method similar to that of described in Example 4, except that butyl alcohol was used in place of methanol, there was obtained 2,3,5-collidine in a yield of 28%.

What is claimed is:

1. A process for producing 2,3,5-collidine and/or 2,3,5,6-tetramethylpyridine, which comprises reacting 3,5-lutidine with an aliphatic alcohol having 1 to 4 carbon atoms in a liquid reaction system at a temperature of 200° C. to 270° C. in the presence of a Raney cobalt catalyst, wherein the aliphatic alcohol is continuously supplied to the reaction system and wherein gas produced during the reaction is removed from the reaction system.

2. A process according to claim 1, wherein the aliphatic alcohol is methanol.

* * * * *